United States Patent [19]

Price et al.

[11] 4,161,577
[45] Jul. 17, 1979

[54] CATIONIC DYEABLE COPOLYESTERS

[75] Inventors: John A. Price, Swarthmore, Pa.; Hugo Stange, Princeton, N.J.

[73] Assignee: Avtex Fibers Inc., Valley Forge, Pa.

[21] Appl. No.: 309,274

[22] Filed: Nov. 24, 1972

Related U.S. Application Data

[63] Continuation-in-part of Ser. No. 43,600, Jun. 4, 1970, abandoned, which is a continuation-in-part of Ser. No. 855,033, Sep. 3, 1969, abandoned.

[51] Int. Cl.$^2$ .................. C08G 63/66; C08G 63/68
[52] U.S. Cl. .................................... 528/173; 528/295
[58] Field of Search .................. 260/49; 528/173, 295

[56] References Cited

U.S. PATENT DOCUMENTS

| | | | |
|---|---|---|---|
| 3,018,272 | 1/1962 | Griffing et al. | 260/75 |
| 3,222,299 | 12/1965 | MacDowell | 260/2.3 |
| 3,238,180 | 3/1966 | Wiloth | 260/47 |
| 3,663,508 | 5/1972 | Mobius et al. | 260/49 |
| 3,806,493 | 4/1974 | Wurmb et al. | 260/49 |

Primary Examiner—Lester L. Lee
Attorney, Agent, or Firm—Arthur R. Eglington

[57] ABSTRACT

Copolyester resins comprising the condensation polymerization product of (a) an aromatic dicarboxylic acid or its lower dialkyl ester (b) an aliphatic glycol and a minor amount of a substituted aromatic acid ester represented by the formula:

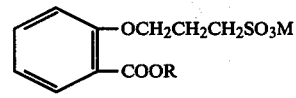

where R is a lower alkyl radical having 1 to 4 carbon atoms and M is an alkali metal from the group consisting of sodium, potassium, and lithium.

3 Claims, No Drawings

CATIONIC DYEABLE COPOLYESTERS

This application is a continuation-in-part of the copending U.S. Pat., Ser. No. 43,600, filed June 4, 1970, which is in turn a continuation-in-part of patent application, Ser. No. 855,033, filed Sept. 3, 1969 both now abandoned.

This invention relates to highly polymeric linear copolyester resins which have improved dyeability. More particularly, the present invention relates to novel, copolyester resins which can be formed into filaments, films, or other shaped articles and which can be readily dyed with basic type dyes. The term "basic dye" is used herein to denote cationic organic dyes such as, for example, those containing sulfonium, oxonium, or quarternary ammonium functional groups.

Many types of random copolyesters have been described in the prior art and they can be prepared by various well-known processes. For example, copolyester resins can be prepared by a direction esterification and polycondensation process or by a transesterification and polycondensation process. In the case of the direct esterification method, the reactants used consist of suitable dicarboxylic acids and diols; whereas, in the transesterification method, lower dialkyl esters of suitable dicarboxylic acids and diols are used as the initial reactants.

A copolyester resin, such as those of the present invention, which are suitable for filament- and film-forming purposes should have relatively high intrinsic viscosity, preferably not less than about 0.50 (as determined in a 60% phenol-40% tetrachloroethane solution, wt./wt., at 30° C.), a carboxyl content value of below about 50 equivalents per million grams (eg./$10^6$ gr. or meg./kg.), a suitable high melting point and also exhibit a relatively colorless or white color. Additionally, especially for filament-forming purposes, it is very desirable and necessary in many instances that the polyester resin be dyeable with cationic or basic dyes.

It is an object of this invention to provide novel highly polymeric saturated copolyester resins.

It is another object of this invention to provide highly polymeric linear copolyester resins which have physical and chemical properties which make them particularly well-suited for filament- and film-forming purposes and which are readily dyeable with cationic or basic dyes.

These and other objects are accomplished in accordance with the present invention by providing a highly polymeric copolyester resin comprising the condensation polymerization product of (a) an aromatic dicarboxylic acid or its lower dialkyl ester, (b) an aliphatic glycol; (a) and (b) making up the primary segments (1) and (c) a minor amount of a substituted aromatic acid ester that makes up the secondary segments (2) and is represented by the formula:

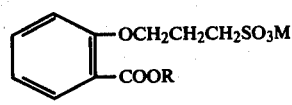

wherein R is a lower alkyl radical having 1 to 4 carbon atoms and M is an alkali metal from the group consisting of sodium potassium or lithium and as shown the carboxylate group is in the ortho or 2 position with respect to the alkoyx sulfonate group.

The following are examples of compounds that may be used:
Sodium 3-(2-carbomethoxyphenoxy) propane sulfonate
Sodium 3-(2-carboethoxyphenoxy) propane sulfonate
Sodium 3-(2-carbopropoxyphenoxy) propane sulfonate
Sodium 3-(2-carbobutoxyphenoxy) propane sulfonate
also the potassium and lithium substituted alkane sulfonates may be used.

The random copolyester resins of the present invention can be prepared as stated above by either a transesterification or direct esterification process. In the former process, all the reactants can be initially combined and charged into a suitable reactor wherein one of the subject processes is carried out. In the latter case, the diacid is completely esterified by the diol before the addition of the alkoxy-sulfonate monomer.

It has been determined that a preferred group of copolyester resins of the present invention are those containing from about 0.5 to 3 mole percent of "secondary segments" represented by (2) above and from about 99.5 to 97 mole percent of "primary segments" represented by (1) above. Obviously, the copolyester resins of the present invention are not limited by such preferred concentrations. Copolyester resins containing smaller or greater concentrations of segment (2) above can also be prepared depending on the physical and chemical properties desired along with depth of dyeability needed.

The aliphatic glycols which can be employed in conjunction with the terephthalic acid or diesters thereof to prepare the polyester of this invention are those having the formula: $HO(CH_2)_zOH$, wherein z is a positive integer of from 2 to 6 and cycloaliphatic glycols such as 1,4-cyclohexane dimethanol. Among the alkylene glycols that can be used to prepare the "primary segments" are, for example, ethylene glycol, 1,4-butylene glycol, and 1,6-hexylene glycol.

The saturated aromatic dibasic acid used as the acid component of the polyester of this invention is terephthalic acid. Obviously, if the transesterification method is utilized to prepare the subject copolyesters, a corresponding lower dialkyl ester of such a dibasic acid would be used instead of free acid. The alkyl groups of such a dialkyl ester can contain from 1 to 4 carbon atoms.

Specifically, the monofunctional sulfonate monomers of the present invention represented by the above general formula can be most readily prepared as follows: A suitable metal compound or an alkali metal is dissolved in methanol to make the corresponding metallic alkoxide. This metallic alkoxide in turn is reacted with a lower alkyl ($C_1$ to $C_4$)o-, hydroxybenzoate at the reflux temperature of the alkanol used for about one hour at atmospheric pressure to form the corresponding lower alkyl hydroxybenzoate metallic salt. The alkanol is then removed from the reaction mixture at reduced pressure to give the corresponding crystalline o-lower alkyl hydroxybenzoate, metallic salt.

A mixture of the above prepared o-, lower alkyl hydroxybenzoate, metallic salt and propane sultone at a mole ratio of 1:1 is placed in a reaction vessel containing a large excess of anhydrous dimethylformamide and refluxed for about 4 hours at the boiling point of the reaction mixture at atmospheric pressure. The resulting mixture is filtered. Then the filtrate is evaporated to dryness in vacuo. The concentrated residue is dissolved in boiling methanol and the resulting mixture is then cooled. The precipitate formed is a lower alkyl o-, (sulfopropoxy)-benzoate, metallic salt, and is isolated by filtering and drying.

To further illustrate the preparation of the monofunctional sulfonate monomers of the present invention, methyl 2-(3-sulfopropoxy) benzoate, sodium salt, can be prepared as follows:

EXAMPLE A

To 11.5 grams (0.5 g.-atoms) of sodium previously dissolved in 500 ml. of absolute methanol was added 76 grams (0.5 mole) of methyl salicylate. This mixture was refluxed for one hour, then concentrated to dryness in vacuo to give methyl saalicylate, sodium salt.

A mixture of 52 grams (0.3 mole) of methyl salicylate sodium salt, prepared above, 36.6 grams (0.3 mole) of 1,3-propane sultone and 500 ml. of anhydrous dimethylformamide was refluxed 4 hours. The reaction mixture was kept at room temperature for 3 days and then filtered. The filtrate was evaporated to dryness in vacuo. The resulting residue was then dissolved in 400 ml. of boiling methanol, treated twice with Norit-Celite and evaporated to 250 ml. After cooling overnight in the refrigerator, the precipitate was filtered and identified as methyl 2-(3-sulfopropoxy)-benzoate, sodium salt.

The other monofunctional sulfonate monomers useful in practicing this invention may be made by this method using the corresponding initial reactants.

The use of this combination of process steps to prepare products containing a phenoxyalkane-sulfonate grouping is known to those skilled in the present art and is disclosed in U.S. Pat. No. 3,238,180.

In the case of the ester-interchange or transesterification method, a mole ratio of diol to suitable diester of from about 1.5:1 to 15:1 may be used, but preferably from about 1.8:1 to about 2.6:1. The transesterification reaction is generally carried out at atmospheric pressure in an inert atmosphere such as nitrogen, initially at a temperature range from about 125° C. to about 250° C. but preferably from about 150° C. to 200° C. in the presence of a transesterification catalyst. The alkyl alcohol corresponding to the dialkyl ester of the dicarboxylic acid used is evolved and continuously removed by distillation. After a reaction period of 1 to 2 hours, the temperature of the reaction mixture is raised from about 200° C. to about 230° C. for approximately 1 to 3 hours in order to complete the reaction, form the desired polyester prepolymer and distill off any excess diol which is present.

Any of the well-known and suitable transesterification or ester-interchange catalysts, for example, calcium acetate, lithium hydride, or zinc acetate can be used to catalyze the present transesterification reaction. In most instances, the transesterification catalyst is used on concentrations ranging from 0.01% to about 0.20% based on the weight of the dialkyl ester of the dicarboxylic acid used in the initial reaction mixture.

Alternatively, the preparation of the subject prepolymers or polyester resins can be achieved via the direct esterification method. In the case of the direct esterification method a mole ratio of diol to dicarboxylic acid of from about 1.2:1 to about 15:1, but preferably from about 1.5:1 to about 2.6:1, is used. The initial steps of the direct esterification reaction are generally carried out at temperatures ranging from about 180° C. to about 280° C. in the absence of an oxygen-containing atmosphere at atmospheric or elevated pressure for about 2 to 4 hours to form the desired polyester prepolymer. For example, the reaction may be carried out in an atmosphere of nitrogen.

Any of the well-known and suitable first stage direct esterification buffers may be used in the preparation of the present copolyester resins. For example, triethylamine or calcium acetate may be used. The buffers are generally employed at concentrations ranging from about $5 \times 10^{-5}$ mole to about $5 \times 10^{-2}$ mole of buffer per mole of dicarboxylic acid used in the initial reaction mixture.

The polycondensation of the prepolymers prepared by one of the above processes is accomplished by adding a suitable polycondensation catalyst to the polyester prepolymer or prepolymers as defined above and heating the blend thereof under reduced pressures of within the range of about 0.05 mm. to 20 mm. of mercury while under agitation at a temperature of about 260° C. to 325° C. for from 2 to 4 hours. Any suitable polycondensation catalyst can be used, for example, antimony oxalate, antimony trioxide, or disodium lead ethylene diamine tetraacetate.

Preferred embodiments of the resins of the present invention are further illustrated by the following examples:

EXAMPLE I

294 Grams of dimethyl terephthalate, 9.0 grams of sodium salt of methyl 2-(3-sulfopropoxy)-benzoate (2 mole percent on diester content). 198 mls. of ethylene glycol, and 0.12 grams of lithium hydride were charged into a reaction vessel equipped with a nitrogen inlet, a distilling arm, heating means and stirring means. The reaction was agitated and heated at atmospheric pressure to about 198° C. under a nitrogen blanket with stirring. The reaction mixture was held at about 198° C. for about 2 hours during which time by-product methyl alcohol was distilled off. Then the temperature of the reaction mixture was allowed to rise to about 230° C. over a period of about 1 hour to distill off any remaining by-product methyl alcohol and thereby to form the desired copolyester prepolymer. The prepolymer was then allowed to cool under an atmosphere of nitrogen.

EXAMPLE II

Fifty grams of the prepolymer product of Example I was mixed with 0.02 grams of antimony trioxide and placed in a reaction vessel. This reaction mixture was then heated at about 280° C. under reduced pressure of about 0.1 mm. of mercury while under agitation for about 1½ hours to bring about the polycondensation of the prepolymer and formation of a copolyester resin.

The polyester resins comprising the other monofunctional sulfonate units in the polymer chains may be made in the same manner using the respective alkoxy sulfonate monomers disclosed.

It is found that the polyester resins of applicants' invention that have copolymerized with, or that have in the polymer chains a minor amount of a substituted aromatic acid or ester having a metal propoxy sulfonate group in a position ortho to the carboxyl or carboxylate residue, give improved or unexpected results over those polyester resins in which a metal alkoxy sulfonate group is in the meta or para position with respect to the carboxyl or carboxylate residue, such as disclosed in the U.S. Pat. No. 3,663,508, to Mobius et al, that issued May 16, 1972. Fibers of polyester resin of applicants' invention have deeper cationic dyeing characteristics or will dye darker than fibers of polyester resins that have an alkoxy sulfonate group in the meta or para position with respect to the carboxyl or carboxylate residue. Also, fibers of the resin of applicants' invention have better textile fiber properties. Three separate polyester resins of ethylene glycol and dimethyl terephthalate and each with two mole percent of one of the following modified hydroxy benzoate esters, which resins will be indicated by the following Code #'s inserted above the respective modified hydroxy benzoate ester, were prepared.

9572

Sodium 3-(4-carboxymethoxyphenoxy) propane sulfonate

9573

Sodium 3-(2-carboxymethoxyphenoxy) propane sulfonate

9835

Sodium 3-(3-carboxymethoxyphenoxy) propane sulfonate

The polyester resin in each case was prepared in much the conventional manner by combining dimethyl terephthalate and the modified hydroxy benzoate ester and ethylene glycol using 2.4 moles of dimethyl terephthalate, 0.5 mole of the modified hydroxy benzoate ester with an amount of ethylene glycol such that the mole ratio of the ethylene glycol to the dimethyl terephthalate and the modified hydroxy benzoate ester is 2.3.

A calcium acetate catalyst in an amount of 0.04 weight percent based on the weight of the dimethyl terephthalate and the modified hydroxy benzoate ester is added to the mixture. This mixture is heated from room temperature to 160° C. and the methanol distilled off. The temperature is then raised to 240° C. and the heating is continued until some ethylene glycol is distilled off. This part of the process is carried out at atmospheric pressure.

A small amount of a condensation catalyst, namely, 0.04% by weight based on the combined weight of the original dimethyl terephthalate and modified hydroxy benzoate ester of antimony trioxide is added. The mixture is gradually heated up to a temperature of 280° C. over a period of from 1 hour to 1½ hours while the pressure is reduced from atmospheric to that of 1 millimeter of mercury. This reaction is carried out until the intrinsic viscosity is obtained.

The resin was spun into fibers which were dyed with Sevron Blue ER dye and the depth of the color was noted. It was observed that fibers of the resin #9573 were acceptably dyed to a suitable blue color while those of the resin #9572 showed merely a light staining, which was not acceptable. In making the resins the reaction mixture was heated for approximately 105 minutes while reducing the pressure from 750 to 0.6 millimeter of mercury. The heating was then continued, and the pressure was further reduced from 0.6 to 0.02 millimeter of mercury. While the resin #9573 embodying applicants' invention reached this stage in 90 minutes, the resin #9835 required 120 minutes. The resin #9835 when formed into filaments and the physical properties were tested, did not produce fibers having the textile properties of resin #9573. The resin #9573 had an intrinsic viscosity of 0.516, while that of resin #9835 was lower, being 0.453. The tenacity of fibers of resin #9573 was 2.99 grams per denier and the elongation 24.6; while fibers of resin #9835 had a lower tenacity and elongation; namely, 2.12 grams per denier and an elongation strength of 20.4. The draw-down to break ratio of fibers of resin #9573 was 6.05 while that of resin #9835 was 5.08.

While preferred embodiments of this invention have been shown and described changed and variations may be made without departing from the spirit of the invention as defined in the appended claims.

We claim:

1. A fiber-forming copolyester resin comprising the condensation polymerization product of terephthalic acid or its lower dialkyl ester, an aliphatic glycol and a substituted aromatic acid ester represented by the

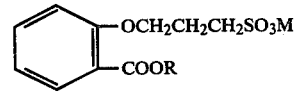

where R is a lower alkyl radical having 1 to 4 carbon atoms and M is an alkali metal selected from the group consisting of sodium, potassium and lithium and the carboxylate group is in the ortho position with respect to the metal propoxy sulfonate group, said substituted aromatic acid ester being present in an amount sufficient to improve the basic dyeability of the copolyester resin.

2. A composition of claim 1 wherein the metal is sodium and R is methyl.

3. A composition of claim 2 wherein the aliphatic glycol is ethylene glycol.

UNITED STATES PATENT AND TRADEMARK OFFICE
CERTIFICATE OF CORRECTION

PATENT NO. : 4,161,577
DATED : July 17, 1979
INVENTOR(S) : John A. Price and Hugo Stange It is certified that error appears in the above-identified patent and that said Letters Patent are hereby corrected as shown below:

Col. 1, line 15, "quarternary" should be "quaternary";
Col. 1, line 20, "direction" should be "direct";
Col. 1, line 34, "eg." should be "eq.";
Col. 1, line 35, "meg." should be "meq.";
Col. 1, line 66, insert "," between "sodium" and "potassium";
Col. 1, line 68, "alkoyx" should be "alkoxy";
Col. 2, line 52, "($C_1$ to $C_4$)O-, hydroxybenzoate" should be "($C_1$ to $C_4$), o-hydroxybenzoate;
Col. 3, line 13, "saalicylate" should be "salicylate";
Col. 4, line 33, insert the word "mixture" after "reaction";
Col. 6, line 24, "changed" should be "changes";
Col. 6, line 32, insert the word "formula" after phrase "by the".

Signed and Sealed this

Eleventh Day of December 1979

[SEAL]

Attest:

SIDNEY A. DIAMOND

Attesting Officer    Commissioner of Patents and Trademarks